(12) United States Patent
Maignan

(10) Patent No.: US 6,414,038 B2
(45) Date of Patent: Jul. 2, 2002

(54) HYDROXYSTILBENES FOR REDUCING/ INHIBITING PROTEIN GLYCATION AND COMBATING SKIN AGING

(75) Inventor: Jean Maignan, Tremblay en (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 09/739,633

(22) Filed: Dec. 20, 2000

(30) Foreign Application Priority Data

Dec. 21, 1999 (FR) ............................................. 99 16168

(51) Int. Cl.⁷ .............................................. A61K 31/05
(52) U.S. Cl. ....................................................... 514/733
(58) Field of Search ......................................... 514/733

(56) References Cited

FOREIGN PATENT DOCUMENTS

EP        1 029 530 A1     8/2000

OTHER PUBLICATIONS

WPIDS An 1999–603260, Breton et al, FR 2 777 186, Oct. 15, 1999, abstract.*

* cited by examiner

Primary Examiner—Rebecca Cook
(74) Attorney, Agent, or Firm—Burns, Doane, Swecker & Mathis, L.L.P.

(57) ABSTRACT

Glycation, particularly of proteins, notably of the skin and/or nails and/or hair of an individual subject in need of such treatment, especially for combating skin aging, comprises administering thereto, for such period of time as required to elicit the desired cosmetic/therapeutic response, a thus-effective amount of at least one hydroxystilbene compound, e.g., of 3,3',5,5'-tetrahydroxystilbene or derivative thereof.

9 Claims, No Drawings

HYDROXYSTILBENES FOR REDUCING/INHIBITING PROTEIN GLYCATION AND COMBATING SKIN AGING

CROSS-REFERENCE TO PRIORITY APPLICATION

This application claims priority under 35 U.S.C. §119 of FR-99/16168, filed Dec. 21, 1999, hereby expressly incorporated by reference.

BACKGROUND OF THE INVENTION

1. Technical Field of the Invention

The present invention relates to the administration of hydroxystilbenzes and particularly to the topical application of 3,3',5,5'-tetrahydroxystilbene or derivative thereof, or composition comprising same, for reducing or even inhibiting the glycation of proteins, particularly proteins of the skin and/or of its related structures, thus combating skin aging.

2. Description of the Prior Art

Glycation is a nonenzymatic process involving a monosaccharide (glucose or ribose) which reacts via the Maillard reaction with an amino group of an amino acid residue (such as, for example, lysine), particularly an amino acid residue of a protein, to form a Schiff base. The latter, after a molecular rearrangement deemed the Amadori rearrangement, may lead, through a succession of reactions, to bridging, particularly intramolecular bridging such as, for example, of the pentosidine type.

This phenomenon increases regularly with age. It is characterized by the appearance of glycation products, the amount and extent of which increase regularly with age. The glycation products include, for example, pyrraline, carboxymethyllysine, pentosidine, crossline, $N^e$(2-carboxyethyl)lysine (CEL), glyoxallysine dimer (GOLD), methylglyoxallysine dimer (MOLD), 3DG-ARG imidazolone, versperlysines A, B, C, threosidine or, alternatively, advanced glycosylation end-products or AGEs.

The glycation of proteins is therefore a universal phenomenon, well known for the skin, particularly for its dermal component, but which also occurs in the annexes or related structures thereof such as the nails or the hair, particularly on the keratins and more generally in any protein system if the conditions required for glycation exist.

The human skin includes two compartments, namely, a superficial compartment, the epidermis, and a deep compartment, the dermis.

The natural human epidermis principally comprises three types of cells which are the keratinocytes, which are in the great majority, the melanocytes and the Langerhans' cells. Each of these cell types contributes, through its specific functions, to the essential role served in the body by the skin.

The dermis provides the epidermis with a solid support. It is also its nourishing component. It principally comprises fibroblasts and an extracellular matrix which itself comprises various extracellular proteins, among which are, in particular, collagen fibers, elastin and various glycoproteins. All of these extracellular components are synthesized by the fibroblasts. Also present in the dermis are leukocytes, mastocytes and tissue macrophages. Finally, the dermis contains blood vessels and nerve fibers.

The fibroblast, by virtue of its activity in the synthesis of the extracellular matrix proteins (proteoglycans, collagen fibers and other structural glycoproteins) is the principal factor in the structural formation of the dermis.

Collagen fibers are responsible for the strength of the dermis. These are very resistant but sensitive to certain enzymes generally designated collagenases. In the dermis, the collagen fibers are fibrils which are firmly attached to each other, thus forming more than ten types of different structures. The structure of the dermis is in great part due to the entanglement of the packed collagen fibers. The collagen fibers participate in the tonicity of the skin.

Collagen fibers are regularly renewed, but this renewal decreases with age, which causes, in particular, thinning of the dermis. It is also accepted that extrinsic factors such as ultraviolet radiation, tobacco and certain treatments (retinoic acid and derivatives, glucocorticoids, vitamin D and derivatives thereof, for example) also elicit an adverse effect on the skin and on its collagen level.

In the dermal component of the skin, glycation occurs principally in the dermis, on the collagen fibers, according to the process described above. The glycation of collagen increases regularly with age, causing a regular increase in the content of glycation products in the skin.

Without wishing to be bound by any particular theory of skin aging, it should be appreciated that other modifications of collagen which may also be a consequence of glycation, such as a reduction in heat denaturation, an increase in the resistance to enzymatic digestion and an increase in intermolecular bridgings, have been demonstrated during skin aging (Tanaka S. et al., 1988, *J. Mol. Biol.*, 203, 495–505; Takahashi M. et al., 1995, *Analytical Biochemistry*, 232, 158–162). Furthermore, modifications due to glycation of certain constituents of the basal membrane, such as collagen IV, laminin and fibronectin have also been demonstrated (Tarsio J F. et al., 1985, *Diabetes*, 34, 477–484; Tarsio J F. et al., 1988, *Diabetes*, 37, 532–539; Sternberg M. et al., 1995, *C.R. Soc. Biol.* 189, 967–985).

Thus, it is understood why, during skin aging, the physicochemical properties of collagen are modified and the latter becomes more difficult to solubilize and more difficult to degrade.

Hence, one of the components of aged skin indeed appears to be glycated collagen.

It is very well known to this art that the skin results from a close association between at least two compartments constituting same, namely, the epidermis and the dermis. The interactions between the dermis and the epidermis are such that it is reasonable to consider that a modification of one can have consequences on the other. It is suspected that the aging of the dermis in particular, with its glycation phenomena, is bound to have consequences on the epidermis which is associated therewith. Thus, during skin aging, the glycation of collagen should result in modifications of the epidermis which necessarily participate in the aging of the epidermis.

Too, if the glycation of proteins of the dermis, particularly of collagen, causes as many damaging consequences on the skin, similar consequences are to be expected of the glycation of proteins on the annexes or related structures of the skin, such as for example the nails and/or the hair and, in fact, on any protein system.

It is thus desirable and important to provide products or active agents which reduce or even inhibit the phenomenon of glycation of proteins.

SUMMARY OF THE INVENTION

It has now surprisingly and unexpectedly been determined that the hydroxystilbenes in general and 3,3',5,5'- tetrahydroxystilbene or derivatives thereof in particular, exhibit the property of reducing or even inhibiting the phenomenon of glycation of proteins and thus elicit an anti-aging effect on human skin and/or nails and/or hair.

DETAILED DESCRIPTION OF BEST MODE AND SPECIFIC/PREFERRED EMBODIMENTS OF THE INVENTION

More particularly according to the present invention, 3,3',5,5'-tetrahydroxystilbene has the structural formula (I):

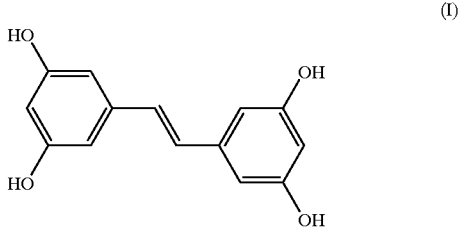

(I)

This compound may be in a Cis- or Trans- form.

The hydroxystilbenes are compounds which exist in the natural state in plants of the class Sphermatophyta and particularly in the vine. Such compounds as, for example, resveratrol exist in grapes and in wine.

In the prior art, hydroxystilbenes are used, inter alia, as depigmenting agents (JP-87/192040), as vasodilating agents (EP-96/830517), as antithrombotic agents (JP-05,016,413), in the treatment of various cardiovascular conditions (CA-2,187,990), as mutagenesis and carcinogenesis inhibiting agents (JP-06,024,967), or, alternatively, have been described as antioxidants.

In this regard, the review by Soleas et al. (*Clinical Biochemistry*, vol. 30, No. 2, pp. 91–113, 1997) perfectly summarizes the state of the art of the hydroxystilbenes.

However, the capacity of 3,3',5,5'-tetrahydroxystilbene or derivatives thereof to reduce or even inhibit the phenomenon of glycation was heretofore unknown.

The present invention thus features the administration of an effective amount of 3,3',5,5'-tetrahydroxystilbene or derivative or composition comprised thereof for reducing or even inhibiting the glycation of proteins, particularly the glycation of proteins of the skin and/or of its annexes/related structures.

By the expression "3,3',5,5'-tetrahydroxystilbene or derivative thereof" are intended 3,3',5,5'-tetrahydroxystilbene itself or one of the O-alkylated or O-acylated derivatives thereof.

By the expression "O-alkylated derivative" is intended that at least one of the phenol functions of 3,3',5,5'-tetrahydroxystilbene is substituted with an alkyl radical. By "alkyl radical" are intended the acyclic radicals obtained via the removal of a hydrogen atom in the molecule of a hydrocarbon, which are linear or branched, optionally substituted, having from 1 to 10 carbon atoms, preferably those having from 1 to 4 carbon atoms, in particular methyl, ethyl, propyl, isopropyl, butyl, isobutyl or tert-butyl radicals and more particularly the methyl radical. By the expression "optionally substituted" is intended an alkyl radical optionally substituted with an amino or hydroxyl radical.

And by the expression "O-acylated derivative" is intended that at least one of the phenol functions of 3,3',5,5'-tetrahydroxystilbene is substituted with an acyl radical having from 1 to 10 carbon atoms, preferably from 1 to 4 carbon atoms, in particular acetyl, propanoyl, isopropanoyl, butanoyl, isobutanoyl, tert-butanoyl radicals. The acyl radical may be optionally substituted with an amino or hydroxyl radical.

This invention also features the topical application of an effective amount of 3,3',5,5'-tetrahydroxystilbene or derivative or composition comprised thereof, for reducing or even inhibiting the glycation of proteins of the dermis, such as, for example collagen, and/or of the nails and/or of the hair, such as for example keratins.

Too, the present invention features the topical application of an effective amount of 3,3',5,5'-tetrahydroxystilbene or derivative or composition comprised thereof for treating, preventively and/or curatively, the signs of aging of the skin or of its annexes or related structures linked to glycation.

Via chemical synthesis, 3,3',5,5'-tetrahydroxystilbene, a known compound, may be prepared according to the technique described in *Journal of Medicinal Chemistry*, 1993, Vol. 36, No. 20, page 2950.

According to the invention, 3,3',5,5'-tetrahydroxystilbene or derivative thereof may be administered alone or in the form of mixtures of any type either with the hydroxyalkylated derivatives or with other hydroxystilbenes and/or their hydroxyalkylated derivatives.

In particular, 3,3',5,5'-tetrahydroxystilbene or derivative or composition comprised thereof is topically applied onto the skin and/or the nails and/or the hair.

The amount of 3,3',5,5'-tetrahydroxystilbene or derivative thereof according to the invention quite obviously depends on the desired effect and should be in a quantity which is effective for reducing or even inhibiting glycation.

For example, the quantity of 3,3',5,5'-tetrahydroxystilbene or derivative thereof according to the invention advantageously ranges from 0.001% to 10% and preferably from 0.005% to 5% of the total weight of the composition comprised thereof.

In addition, the composition of the invention is administered for such periods of time sufficient to elicit the desired effects. To provide an order of magnitude, this duration may be a minimum of 3 weeks, but may also be more than 4 weeks, or even more than 8 weeks.

The subject compositions are well suited for cosmetic or dermatological applications, advantageously for cosmetic use.

The compositions of the invention suited for topical application contain a physiologically acceptable medium (vehicle, diluent or carrier), namely, compatible with the skin including the scalp, its annexes, the mucous membranes and/or the eyes and may constitute, in particular, a cosmetic or dermatological composition.

Such compositions may be provided or formulated in all of the galenic forms normally used in the cosmetic and dermatological fields, and they may, in particular, be in the form of an optionally gelled aqueous solution, an optionally two-phase dispersion of the lotion type, an emulsion obtained by dispersing a fatty phase in an aqueous phase (O/W) or conversely (W/O), or a triple emulsion (W/O/W or O/W/O) or a vesicular dispersion of the ionic and/or nonionic type. These compositions are formulated according to conventional techniques.

The compositions of the invention may constitute, for example, a lotion, a gel, an ointment, a cream or a milk, or, for example, a makeup-removing or cleansing lotion or milk, a shampoo or a shower gel.

This invention also features a cosmetic regimen for treating or combating the signs of aging linked to the glycation of proteins, particularly of the skin and/or the nails and/or the hair, comprising topically applying onto the skin and/or the nails and/or the hair a cosmetic composition comprising an effective amount of 3,3',5,5'-tetrahydroxystilbene or derivative thereof, for inhibiting glycation.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Study of the effect of 3,3',5,5'-tetrahydroxystilbene on glycation, compared with the effect elicited by resveratrol:

A solution of bovine serum albumin at 1 mg/ml in solution in phosphate buffered saline (PBS) was incubated at 37° C. for 14 days in the presence or in the absence of D-ribose at the concentration of 10 $\mu$M, of 3,3',5,5'-tetrahydroxystilbene or of resveratrol, each at the concentrations of 1 $\mu$M and 10 $\mu$M.

The glycation was evaluated by measuring the fluorescence of the AGEs at $\lambda$em.=440 nm emitted by each sample after excitation at $\lambda$ex.=370 nm.

The inhibition of glycation was visualized by the reduction in the fluorescence compared with the sample treated with the sugar alone.

The results obtained were as follows:

|  | A: 1 $\mu$M | B: 1 $\mu$M | A: 10 $\mu$M | B: 10 $\mu$M |
| --- | --- | --- | --- | --- |
| % inhibition | 7.1% | 7.1% | 14.3% | 7.1% |

A: 3,3',5,5'-tetrahydroxystilbene
B: resveratrol 3,3',5,5'-Tetrahydroxystilbene evaluated an advantageous antiglycation effect from the concentration of 1 $\mu$M.

This effect was at least equal to that of resveratrol in low concentration and appeared 2-times higher at the concentration of 10 $\mu$M.

EXAMPLE 2

The following formulations are specific examples of compositions according to the invention. These compositions were formulated by simply intimately admixing the different components thereof.

| Composition 1/Makeup removing lotion for the face: | |
| --- | --- |
| 3,3',5,5'-tetrahydroxystilbene | 0.05% |
| Antioxidant | 0.05% |
| Isopropanol | 40.00% |
| Preservative | 0.30% |
| Water qs | 100.00% |

| Composition 2/Shampoo: | |
| --- | --- |
| 3,3',5,5'-tetrahydroxystilbene | 1.00% |
| Hydroxypropylcellulose (Klucel H ® marketed by Hercules) | 1.00% |
| Sodium lauryl sulfate | 12.00% |
| Perfume | 0.50% |
| Preservative | 0.30% |
| Water qs | 100.00% |

| Composition 3/Care cream for the face (oil-in-water emulsion): | |
| --- | --- |
| 3,3',5,5'-tetrahydroxystilbene | 0.005% |
| Glyceryl stearate | 2.000% |
| Polysorbate 60 (Tween 60 ® marketed by ICI) | 1.000% |
| Stearic acid | 1.400% |
| Triethanolamine | 0.700% |
| Carbomer | 0.400% |
| Liquid fraction of shea butter | 12.000% |
| Perhydrosqualene | 12.000% |
| Antioxidant | 0.050% |
| Perfume | 0.500% |
| Preservative | 0.300% |
| Water qs | 100.00% |

| Composition 4/Skin gel: | |
| --- | --- |
| 3,3',5,5'-tetrahydroxystilbene | 2.00% |
| All-trans-retinoic acid | 0.05% |
| Hydroxypropylcellulose (Klucel H ® marketed by Hercules) | 1.00% |
| Antioxidant | 0.05% |
| Isopropanol | 40.00% |
| Preservative | 0.30% |
| Water qs | 100.00% |

| Composition 5/Care gel for the face: | |
| --- | --- |
| 3,3',5,5'-tetrahydroxystilbene | 0.01% |
| Hydroxypropylcellulose (Klucel H ® marketed by Hercules) | 1.00% |
| Antioxidant | 0.05% |
| Isopropanol | 40.00% |
| Preservative | 0.30% |
| Water qs | 100.00% |

| Composition 6/Gel: | |
| --- | --- |
| 3,3',5,5'-tetrahydroxystilbene | 0.10% |
| Hydroxypropylcellulose (Klucel H ® marketed by Hercules) | 1.00% |
| Antioxidant | 0.50% |
| Lidocaine hydrochloride | 2.00% |
| Isopropanol | 40.00% |
| Preservative | 0.30% |
| Water qs | 100.00% |

| Composition 7/Care cream (oil-in-water emulsion): | |
| --- | --- |
| 3,3',5,5'-tetrahydroxystilbene | 5.00% |
| Glyceryl stearate | 2.00% |
| Polysorbate 60 (Tween 60 ® marketed by ICI) | 1.00% |
| Stearic acid | 1.40% |
| Glycyrrhetinic acid | 2.00% |
| Triethanolamine | 0.70% |
| Carbomer | 0.40% |
| Liquid fraction of shea butter | 12.00% |
| Sunflower oil | 10.00% |
| Antioxidant | 0.05% |
| Perfume | 0.50% |
| Preservative | 0.30% |
| Water qs | 100.00% |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for at least one of reducing and inhibiting glycation in an individual subject in need of said method, comprising administering thereto, for a period of time as required to elicit at least one of a reduction and an inhibition of said glycation, an effective amount of at least one 3,3',5,5'-tetrahydroxystilbene compound or O-alkyl or O-acyl derivative thereof.

2. The method as defined by claim 1, comprising at least one of reducing and inhibiting the glycation of proteins.

3. The method as defined by claim 2, comprising at least one of reducing and inhibiting the glycation of proteins of at least one of the skin, the nails and the hair.

4. The method as defined by claim 3, comprising at least one of reducing and inhibiting the glycation of proteins of the dermis of the skin.

5. The method as defined by claim 3, comprising at least one of reducing and inhibiting the glycation of collagen.

6. The method as defined by claim 3, comprising at least one of reducing and inhibiting the glycation of keratins.

7. A method as defined by claim 1, comprising topically applying onto at least one of the skin, the nails, and the hair of said individual subject, a composition which comprises from 0.001% to 10% by weight of said at least one 3,3',5,5'-tetrahydroxystilbene compound or derivative thereof, formulated into a topically applicable, physiologically acceptable vehicle, diluent or carrier therefor.

8. A method as defined by claim 7, said composition comprising from 0.005% to 5% by weight of said at least on 3,3',5,5'-tetrahydroxystilbene compound or derivative thereof.

9. The method as defined by claim 7, said composition comprising a gel, a lotion, an emulsion, a vesicular dispersion, an ointment, a cream, a milk, or a shampoo.

* * * * *